US009820986B2

(12) United States Patent
Wei et al.

(10) Patent No.: US 9,820,986 B2
(45) Date of Patent: Nov. 21, 2017

(54) GLYCOPEPTIDE COMPOSITIONS

(75) Inventors: I-Chien Wei, San-Ming District (TW);
David J. Yang, Sugarland, TX (US);
Dong-Fang Yu, Houston, TX (US)

(73) Assignees: TAIWAN HOPAZ CHEMS, MFG. CO., LTD., Daliao, Kaohsiung (TW);
BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 1027 days.

(21) Appl. No.: 11/071,975

(22) Filed: Mar. 4, 2005

(65) Prior Publication Data

US 2006/0198786 A1 Sep. 7, 2006

(51) Int. Cl.
*A61K 31/505* (2006.01)
*A61K 31/66* (2006.01)
*A61K 51/02* (2006.01)

(52) U.S. Cl.
CPC ............ *A61K 31/505* (2013.01); *A61K 31/66* (2013.01); *A61K 51/025* (2013.01)

(58) Field of Classification Search
USPC ...................................................... 424/1.69
See application file for complete search history.

(56) References Cited

U.S. PATENT DOCUMENTS

| 4,010,251 A | 3/1977 | Green ............................ 424/1.5 |
| 4,699,784 A | 10/1987 | Shih ................................ 424/85 |
| 6,835,393 B2 * | 12/2004 | Hoffman et al. ............. 424/450 |
| 6,852,696 B2 * | 2/2005 | Takashima et al. ............ 514/13 |
| 2003/0175208 A1 * | 9/2003 | Yu et al. ........................ 424/1.49 |
| 2004/0018960 A1 | 1/2004 | Li et al. .............................. 514/2 |
| 2006/0182687 A1 * | 8/2006 | Yang et al. ................. 424/9.364 |

FOREIGN PATENT DOCUMENTS

| AU | 72637/91 | 6/1991 | ............. C06B 37/00 |
| EP | 0446143 A2 | 3/1991 | ............. C08B 37/00 |
| EP | 1155702 A1 | 11/2001 | ............. A61K 47/48 |
| EP | 1609797 A1 | 12/2005 | ............. C07H 15/04 |
| WO | 87/05330 | 9/1987 | ............. C12P 21/00 |

OTHER PUBLICATIONS

Li (Adv. Drug Delivery Rev. 2002, 54, 695-713).*
Blok et al. (Eur. J. Nucl. Med. 1999, 26, 1511-1519).*
Margaritis et al. (Critical Reviews in Biotechnology 2001, 21, 219-232).*
Wei-Chiang Shen et al. "Disulfide Spacer Between Methotrexate and Poly(D-lysine)" *Journal of Biological Chemistry, American Society of Biochemical Biologists*, vol. 260, No. 20 (pp. 10905-10908), Sep. 15, 1985.
Makiya Nishikawa et al. "Synthesis and Pharmacokinetics of a New Liver-Specific Carrier, Glycosylated Carboxymethyl-Dextran, and its Appliction to Drug Targeting" *Pharmaceutical Research*, vol. 10, No. 9 (pp. 1253-1261), 1993.
Hideo Nogusa et al. "Synthesis of Carboxymethylpullulan-Peptide-Doxorubicin Conjugates and Their Properties" *Chemical and Pharmaceutical Bulletin, Pharmaceutical Society of Japan*, vol. 43, No. 11 (pp. 1931-1936), Jan. 11, 1995.
Jayant Khangare et al. "Polymer-Drug Conjugates: Progress in Polymeric Prodrugs" *Progress in Polymer Science, Pergamon Press, Oxford*, vol. 31, No. 4 (pp. 359-397), Apr. 1, 2006.
European Search Report for Application No. EP06004026 (7 pages), dated Jul. 10, 2006.
Extended European Search Report for European Application No. 06004026 (11 pages), dated Nov. 27, 2006.
Communication pursuant to Article 94(3) EPC for European Application No. 06004026 (5 pages).
European Office Action; Application No. 06 004 026.8-2123; pp. 4, dated Jan. 24, 2013.
"99mTc-glycopeptide: Synthesis, biodistribution and imaging in breast tumor-bearng rodents" by I-Chien Wei et al. at ScientDirect, Applied Radiation and Isotopes 66 (2008) 320-331.
European Office Action; Application No. 06 004 026.8-2123; pp. 3, dated Mar. 18, 2016.
European Office Action for Application No. 06 004 026.8, 4 pages, dated Jun. 4, 2008.

* cited by examiner

*Primary Examiner* — Michael G Hartley
*Assistant Examiner* — Melissa J Perreira
(74) *Attorney, Agent, or Firm* — Baker Botts L.L.P.

(57) ABSTRACT

The invention include glycopeptides having a glycoside and a peptide covalently bound through an amide bond. The glycopeptides may also include a diagnostic or therapeutic agent bound to the glycopeptide. A metal, such as a radionuclide, may also be chelated to the glycopeptide. Specific embodiments of the invention relate to glycopeptides made of chitosan covalently bound to a poly(amino acid) such as poly(glutamic acid) or poly(aspartic acid). Diagnostic agents conjugated to the glycopeptide may facilitate imaging. Specific therapeutic agents that may be conjugated to the glycopeptide include anticancer drugs, rheumatoid arthritis drugs, anticoagulants, anti-angiogenesis drugs, apoptosis drugs, osteoporosis drugs, steroids, and anti-inflammatory drugs. Some agents, such as radionuclides, may have both diagnostic and therapeutic effects. The glycopeptides may be made by combining a glycoside and a peptide in the presence of a carbodiimide and an acid group activator to form an amide bond between the glycoside and the peptide.

16 Claims, 8 Drawing Sheets
(3 of 8 Drawing Sheet(s) Filed in Color)

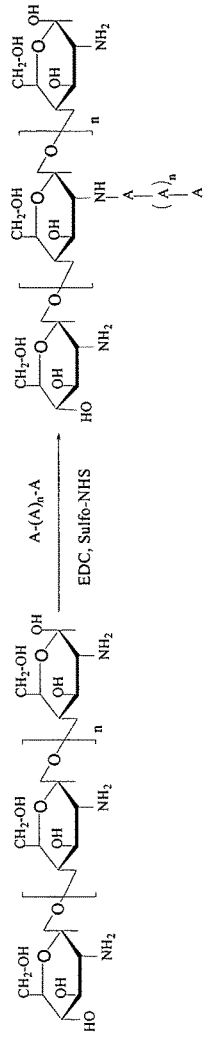
FIGURE 2A
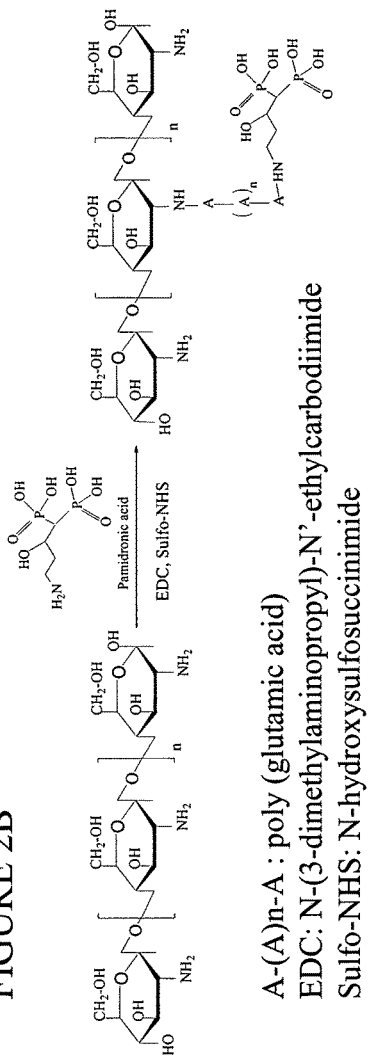
FIGURE 2B
A-(A)n-A : poly (glutamic acid)
EDC: N-(3-dimethylaminopropyl)-N'-ethylcarbodiimide
Sulfo-NHS: N-hydroxysulfosuccinimide
FIGURE 2

| Agent | Glycoside | Peptide | Metal |
|---|---|---|---|

| Metal | Glycoside | Peptide | Agent |
|---|---|---|---|

FIGURE 3

FIGURE 6
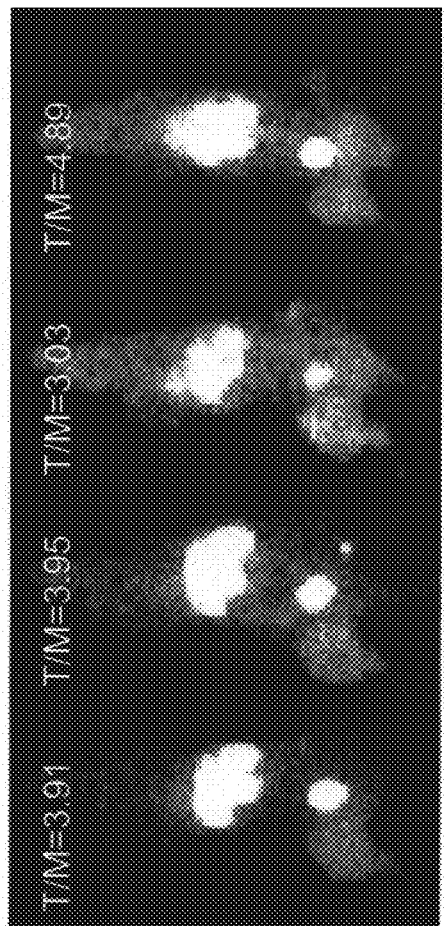
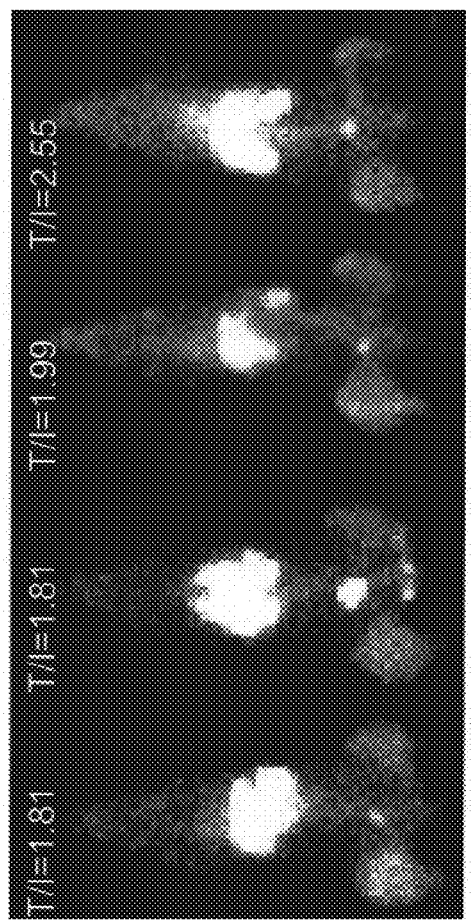

GLYCOPEPTIDE COMPOSITIONS

FIELD OF THE INVENTION

The present invention relates to glycopeptide compositions containing a glycoside and a peptide and their uses as biomaterials. Specific embodiments relate to chitosan-based glycopeptides. More specific embodiments relate to glycopeptides including chitosan and poly(amino acids).

BACKGROUND

Biomaterials are constantly in demand for a variety of medical uses in biological systems, such as humans and other mammals. These medical uses span almost the entire breadth of medical treatments currently possible. For example, some biomaterials are used in medical devices or implants both for structural and biochemical purposes. Others are used as drug delivery vehicles or even as drugs themselves.

The intended use often influences the type of material selected, but in most uses a biodegradable or bioclearable material is preferred. Similarly, while some degree of toxicity or harmfulness may be tolerated or even preferred for certain biomaterials, in most applications it is preferable that the material not be toxic.

Given the wide variety of uses and desired characteristics for biomaterials, there is a constant demand for new biomaterials.

SUMMARY

The present invention relates to glycopeptides formed from at least one glycoside covalently bound to at least one peptide. Although glycosides and peptides, as well as agents conjugated thereto are often referred to in the singular throughout the specification and claims, given the polymeric nature of the present invention, it will be readily understood by one skilled in the art that glycopeptides may contain more than one glycoside and more than one peptide. Further, because of multiple binding sites, many agents of a given type may be bound to a single glycopeptide. Methods to control the relative numbers of glycopeptide monomers as well as the degree of substitution of any agents on polymers are well known in the art and may be applied to the present invention through routine experimentation.

In one embodiment, the invention includes a glycopeptide having at least one glycoside moiety covalently bound through an amide bond to at least one peptide and additionally a diagnostic or therapeutic agent conjugated to one of either the glycoside or peptide moiety. Further, the glycopeptide may have a metal agent conjugated to the moiety not having a diagnostic or therapeutic agent.

The diagnostic or therapeutic agent may be conjugated to the glycoside through a carboxylic acid via a peptide bond linkage, in which case any metal may be chelated to the peptide. Alternative, the diagnostic or therapeutic agent may be conjugated to the peptide through an amine group via a peptide bond linkage, in which case any metal may be chelated to the glycoside. The glycopeptide may have a molecular weight of about 5,000 daltons to about 30,000 daltons.

The glycoside may include at least two covalently bound monomeric units. Further, the glycoside may include an aminated sugar. Specifically, the glycoside may be chitosan, collagen, chondroitin, hyauraniate, and heparin, and any combinations thereof. The glycoside may be selected based on ability to target endothelial cells such as vascular tissue, including extracellular proteins of vascular tissue, such as integrins. The glycoside may have a molecular weight of from about 3,000 daltons to about 10,000 daltons.

The peptide may include a poly(amino acid) or a peptide or a given targeting sequence. Poly(amino acids) having primarily acidic amino acids may be preferred in some embodiments. The poly(amino acid) may include poly(glutamic acid) and poly(aspartic acid), and any combinations thereof. The peptide may make up about 5% to about 50% by weight of the glycopeptide. Further, the peptide may have a molecular weight of from about 750 daltons to about 3,000. The peptide may target cancer cells.

The diagnostic or therapeutic agent may make up from about 10% to about 60% by weight of the glycopeptide. Any diagnostic or therapeutic agent capable to be conjugated to the glycopeptide may be used. In certain embodiments, the diagnostic agent may be an anticancer drug, rheumatoid arthritis drug, anticoagulant, anti-angiogenesis drug, apoptosis drug, osteoporosis drug, steroid, anti-inflammatory drug, or any combination thereof. For example, the diagnostic or therapeutic agent may include methotrexate or pamidronate.

In some embodiments, the glycopeptide may also include an additional metal diagnostic or therapeutic agent. Specifically, the metal may be conjugated via a chelating agent, such as DPTA. The metal may be a radionuclide, such as Tc-99m, Cu-60, Cu-61, Cu-62, Cu-67, In-111, Tl-201, Ga-67, Ga-68, As-72, Re-186, Re-188, Ho-166, Y-90, Sm-153, Sr-89, Gd-157, Bi-212, and Bi-213, or any combinations thereof. Radionuclide metals may serve a dual purpose as both a diagnostic and a therapeutic.

Diagnostic agents may facilitate diagnosis in a variety of manners, including imaging. In some embodiments, the glycopeptides may be used for combined diagnosis and treatment and for dosage measurement in a subject. The may be accomplished by using a radionuclide, which both facilitates imaging and serves as an anti-cancer agent. Alternatively, the glycopeptide may include a metal and a therapeutic agent, allowing one to measure the amount of the therapeutic delivered to the target area in a subject. In yet another alternative, two different glycopeptides may be used in combination. First, a diagnostic glycopeptide may be administered to a subject and the amount reaching the target area measured. Next, the correct dosage for a therapeutic glycopeptide may be determined based on the assumption that it will reach the target area in amounts similar to the diagnostic glycopeptide.

Other embodiments of the present invention relate to a glycopeptide including a chitosan covalently bound to a poly(amino acid) via an amide bond. The chitosan may be an unmodified chitosan, or a modified version, such as alkyl sulfonated chitosan. Similarly, the poly(amino acid) may be of any type, but in many embodiments it may be an acidic poly(amino acid) such as poly(glutamic acid) or poly(aspartic acid).

Chitosan-based glycopeptides of the present invention may be used in the same manner as glycopeptides of the present invention described above. For example, chitosan-based glycopeptide may also have a diagnostic or therapeutic agent, including a metal, conjugated thereto.

Other embodiments of the present invention relate methods of making glycopeptide, such as those described above. Specifically, a glycoside and a peptide may be combined in the presence of a carbodiimide and an acid group activator to form an amide bond between the glycoside and peptide. The glycoside may be further reacted to form an amide or ester bond between the glycoside or peptide and a diagnostic or therapeutic agent. Additionally, a chelating agent may be conjugated to the glycoside or peptide to allow chelation of a metal.

BRIEF DESCRIPTION OF THE DRAWINGS

A more complete and thorough understanding of the present embodiments and advantages thereof may be acquired by referring to the following description taken in conjunction with the accompanying drawings. The patent or application file contains at least one drawing executed in color. Copies of this patent or patent application publication with color drawing(s) will be provided by the Office upon request and payment of the necessary fee.

FIG. 2 illustrates a synthesis reaction for formation of glycopeptide (FIG. 2A) and glycopeptide conjugates (FIG. 2B).

FIG. 3 illustrates two different glycopeptide conjugates having both a metal and another agent conjugated to the glycopeptide.

FIG. 6 shows the results of assays for cellular uptake in breast cancer cells (13762 cell line) in vivo. Planar scintography of $^{99m}$Tc-CH-10(50%), $^{99m}$Tc-CH-10(100%), $^{99m}$Tc-PGA(750) and $^{99m}$Tc-G-P(1:2) in breast tumor cell line and inflammation-bearing rats (280-300 mCi/rat, i.v. injection, acquired 500,000 count) was performed 120 minutes after injection to compare tumor visualization. Tumor-to-Muscle and Tumor-to-inflammation ratios are shown. T=tumor, M=muscle and I=Inflammation.

DETAILED DESCRIPTION

The present invention relates to glycopeptide (GP) compositions containing a glycoside and a peptide and their uses as biomaterials. In some embodiments, these biomaterials may be provided as a sterilized powder. Therapeutic or diagnostic agents may be conjugated to the glycopeptides.

In a specific embodiment, the glycoside and peptide may be joined by an amide bond. The glycoside may be an aminated sugar. The glycopeptide may include between 5% to 50% peptide by weight. Too much peptide may result in unacceptable levels of crosslinking between glycopeptides. The glycoside may have a molecular weight of between about 3,000 to 10,000 daltons. The peptide may have a molecular weight of between about 750 to 3,000 daltons. The glycopeptide may have a molecular weight of between about 5,000 to 30,000 daltons.

In a more specific embodiment, the glycopeptide may be made from chitosan and a poly(amino acid), particularly poly(glutamic acid). This glycopeptide has a tumor targeting capacity without the need for modification to include specific targeting agents.

Chitosan (CH) is a polyaminosaccharide of particular interest in a number of applications. Like many polyaminosaccharides, chitosan may be readily harvested from naturally occurring materials. The primary source of chitosan is presently discarded shells of lobsters and crayfish or shrimp, although it may also be obtained from the shells of crabs and other crustaceans as well as from insect shells and fungi. Chitosan is normally non-toxic and is compatible with a variety of living systems, including human tissues. However, like many other polyaminosaccharides, chitosan exhibits only limited solubility in water. To improve solubility, alkyl sulfonated chitosan may be used. Alkyl sulfonated chitosan is described, for example in U.S. patent application Ser. No. 10/871,890, filed Jun. 18, 2004.

Other suitable glycosides include collagen, chondroitin, hyauraniate and heparin.

Poly(glutamic acid) (PGA) is also readily available commercially (Sigma Chemical Company, St. Louis, Mo.) and may be synthesized in a variety of manners. PGA has a positive charge in physiological conditions and is biodegradable, which may make it more compatible with biological uses.

Other peptides may be used in alternative embodiments of the invention. These peptides may include other poly(amino acids) as well as peptides have a specific sequence or specific amino acid composition. In some embodiments, the peptide may serve a targeting function. In a specific embodiment, poly(aspartic acid) may be used. This likely enhances uptake by tumor cells because they cannot manufacture aspartic acid internally and much obtain it from an external source. For poly(amino acids) including amino acids having an acid group, the acid group may be used for later conjugation of the glycopeptide to various agents or it may be used for salt formation to improve solubility.

Figure 1:
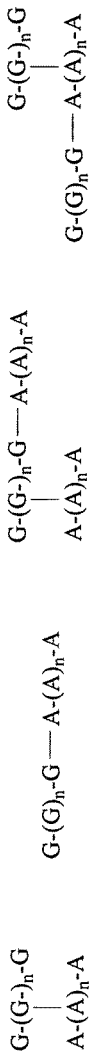
FIG. 1 illustrates glycopeptide compositions comprising glycosides and peptides using chitosan and poly(glutamic acid) as examples in four types of arrangements depicted as FIG. 1A, FIG. 1B, FIG. 1C and FIG. 1D.

Glycopeptides of the present invention may have the glycoside and peptide in a variety of arrangements. Four arrangements using chitosan and poly(glutamic acid) are show in FIG. 1. In various embodiments of the present invention, these different types of glycopeptides may be used as mixtures, or one or more structural arrangement may be separated and used. Whether such separation of a particular structural arrangement is desirable may depend upon many factors, including the intended end use and any conjugates to be added. In most synthesis methods, the structure shown in FIG. 1A is likely to predominate.

One method of synthesizing a glycopeptide of the present invention is show in FIG. 2. Alternative means of synthesis are possible. For example, the synthesis reaction may be designed to favor one type of glycopeptide structure. In specific embodiments such as those shown in FIG. 2, the glycoside and peptide are conjugated using a carbodiimide as a coupling agent. Sulfo-NHS, in FIG. 2, serves as an acid group activator, facilitating glycopeptide formation. Other acid group activators may also be used to form glycopeptides of the present invention.

While the glycopeptides of the present invention may exhibit useful biological properties on their own, a large variety of agents may also be conjugated to the glycopeptides. Relevant agents include targeting, imaging and therapeutic agents. Multiple agents or types of agents may be conjugated to the same glycopeptide molecule at the same time. In specific embodiments, the agent may comprise 10% to 60% by weight of the glycopeptide conjugate.

Although the glycopeptide inherently targets tumor tissue, agents to further increase tumor targeting or to make it more specific may be conjugated. Agents to target other tissue, such as pamidronate to target bone, may also be conjugated. Methotrexate may be used to target folate receptors. Many imagining agents include metals that may be provided by first conjugating a chelating agent, such as DPTA. These may be used to chelate valent metal ions such as $^{99m}$Tc, $^{60}$Cu, $^{61}$Cu, $^{62}$Cu, $^{67}$Cu, $^{111}$In, $^{201}$Tl, $^{67}$Ga, $^{68}$Ga, $^{72}$As, $^{186}$Re, $^{188}$Re, $^{166}$Ho, $^{90}$Y, $^{153}$Sm, $^{89}$Sr, $^{157}$Gd, $^{212}$Bi, and $^{213}$Bi. These metal chelates may be used to image disease lesions. In some embodiments, the carboxyl and amino groups of the glycopeptide itself may be sufficient to chelate metal ions.

Therapeutic agents are most likely to be specific for the targeted tissue, such as chemotherapeutics and other anti-cancer drugs when tumors are targeted. Rheumatoid arthritis, anticoagulant, anti-angiogenesis, apoptosis, steroid, anti-inflammatory, and osteoporosis therapeutics may also be conjugated Therapeutic agents may be conjugated in any acceptable manner, but biolabile bonds, such as amide or ester bonds, may be used in many embodiments. FIG. 2B illustrates one method of conjugating an osteoporosis therapeutics, pamidronate. The same or similar methods may be used to conjugate other agents. Agents may be conjugated to the glycopeptide using either a carboxylic acid or an amine group on the agent. Particularly when water-insoluble agents are conjugated, DMF or DMSO may be added to the reaction.

In specific embodiments, both imaging and therapeutic conjugates may be provided to a subject. The imaging complex may then be used to determine the optimal or recommended dosage of unlabeled therapeutic complex based on how much of the imaging complex localizes to the target areas.

Some imaging complexes may use small metal ions that also have radiotherapeutic effects. These complexes may be imaged to directly determine internal radiotherapeutic dosages in a subject.

Similarly, if radiochemicals or other imaging agents are incorporated in the same complex as a therapeutic agent, dosage of the therapeutic agent in the subject may be directly measured. Examples of such complexes are shown in FIG. 3.

Conjugation of agents to the glycopeptide may provide for sustained release of the agents, particularly in a biological system, such as a mammal. Conjugation may also increase the effective water-solubility and therapeutic index of agents that are poorly water soluble.

Tumor-Related Applications

Embodiments of the present invention may be used to treat tumors, particularly through delivery of cytotoxic agents. Delivery of cytotoxic agents, as opposed to merely cytostatic agents, has often proved problematic in previous treatments. Although the glycopeptides of the present invention may be used to deliver cytostatic agents, the ability of many of them to deliver cytotoxic agents as well increase their value as a therapy vehicle.

In specific embodiments, the glycopeptide used contains chitosan and either poly(glutamic acid) or poly(aspartic acid). These embodiments target tumor tissues, most likely through angiogenesis, which occurs at a vastly increased rate in tumor tissue. Vascular cells, and particularly the integrin molecules located on them, are targeted by poly-saccharides (e.g. collagen, chondroitin, hyauraniate, chitosan). This vascular targeting helps prevent drug resistance of tumor cells because it does not target tumor tissue directly. Additionally, tumor tissue exhibits an increased need for amino acids and most cells have surface receptors for certain amino acids, such as glutamic acid and aspartic acid, allowing the poly(amino acid) portion to serve a targeting function as well. Specifically, the poly(amino acid) is most likely taken up by the tumor cells.

The tumor targeting capacity of glycopeptides of the present invention has been shown with gamma imaging using a $^{99m}$Tc-labeled chitosan/poly(glutamic acid) glycopeptide. $^{99m}$Tc-labeled chitosan/poly(glutamic acid) glycopeptide may be used to quantify the dose needed fro treatment. Ultimately, $^{99m}$Tc-labeled chitosan/poly(glutamic acid) glycopeptide may predict patients who may respond to therapy and be used in their selection. $^{188}$Re may also be used as a radiotherapeutic to treat many tumors. $^{188}$Re is most effective if it remains with the glycoside whether in the vasculature or internalized into a tumor. $^{188}$Re is a beta and gamma (15%) emitter and has a half life of 17 hours. The tissue penetration is 5-7 mm, which can be used to both image and treat large tumors at the same time.

The targeting capacity assists in the delivery of chemotherapeutics with poor water solubility and can thus increase the therapeutic index (toxicity/efficacy) of such agents. Additionally, because the therapeutics are gradually released from the glycopeptide, this also contributes to the therapeutic index and helps lessen acute systemic toxicity.

Bone-Related Applications

In specific embodiments, a pamidronate may be conjugated to a glycopeptide of the present invention. This method of conjugation is show in FIG. 2. Pamidronate is an osteoclast agent. Insignificant toxicity was observed using chitosan/poly(glutamic acid) with pamidronate conjugated. Pamidronate exhibited quick renal clearance. Imagining studies have shown that this composition targets bone. These compositions may be used to treat bone degeneration diseases, such as osteoporosis.

The following examples are provided to further describe selected embodiments of the present invention.

EXAMPLES

Example 1: Synthesis of Glycopeptide

During hydrolysis of chitosan, various molecular weights and percentages of amino group conversions were prepared. Molecular weight and percentage amino group conversions are noted herein as "CH[molecular weight] [amino conversion]%". For example, CH10 designates chitosan with a molecular weight of 10,000 with 100% hydrolysis of the acetamide group to form an amino group.

In a typical synthesis, to a stirred solution of chitosan (CH10, 100%), (200 mg, MW. 10,000-20,000) in water (5 ml), sulfo-NHS (232.8 mg, 1.07 mmol) and 3-ethylcarbo-diimide 1-ethyl-3-(3-dimethylaminopropyl) carbodiimide-HCl (EDC) (204.5 mg, 1.07 mmol) (Pierce Chemical Company, Rockford, Ill.) were added. Poly(glutamic acid) (400 mg, MW. 750-3,000) was then added. The mixture was stirred at room temperature for 24 hours. The mixture was dialyzed for 48 hours using Spectra/POR molecular porous membrane with cut-off at 10,000 (Spectrum Medical Industries Inc., Houston, Tex.). After dialysis, the product was filtered and frozen dried using lyophilizer (Labconco, Kansas City, Mo.). The glycopeptide in the salt form weighed 568.8 mg. The compositions of four types of resulting glycopeptides are shown in FIG. 1. The glycopeptide mixture was used in the remainder of these examples, although isolation and independent use of, for example, each of the four types of glycopeptides, is possible.

Example 2: Radio Labeling of Glycopeptide with $^{99m}$Tc

Glycopeptide (5 mg) was dissolved in 0.2 ml of water and tin chloride (0.1 mg in 0.1 ml of water) was added at room temperature. Sodium pertechnetate (5 mCi) was added. Radiochemical purity was determined by TLC (ITLC SG, Gelman Sciences, Ann Arbor, Mich.) eluted with Methanol: Ammonium acetate (1:4). From radio-TLC (Bioscan, Washington, D.C.) analysis, the radiochemical purity was more than 95%.

Example 3: Synthesis of Glycopeptide-Pamidronate Conjugates

Pamidronate (100 mg, 0.24 mmol) was dissolved in 1 ml of sodium bicarbonate (1N), sulfo-NHS (91.8 mg, 0.43 mmol) and 3-ethylcarbodiimide 1-ethyl-3-(3-dimethylaminopropyl) carbodiimide-HCl (EDC) (81.2 mg, 0.43 mmol). A solution of glycopeptide (200 mg) in 5 ml of deionized water was added. The solution was left stirring for 24 hr at room temperature. After dialysis (MW:10,000) and lyophilization, the yield of pamidronate-glycopeptide was 250 mg. The synthesis scheme is shown in FIG. 2.

Example 4: In Vitro Cell Culture Assay

Figure 4:
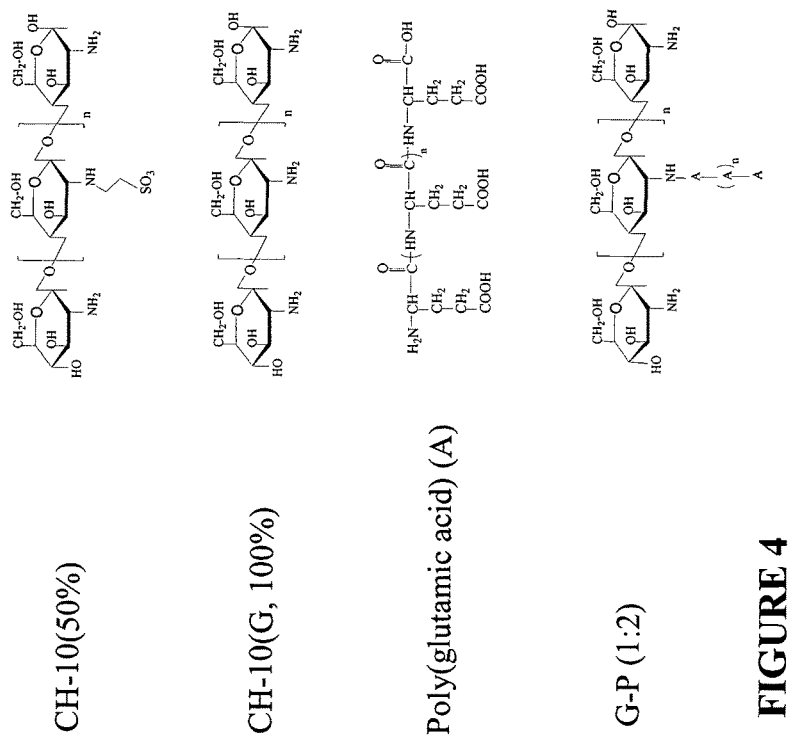
FIG. 4 illustrates structures of the glycopeptide and chitosan agents tested for tumor and bone localization ability.
Figure 5:
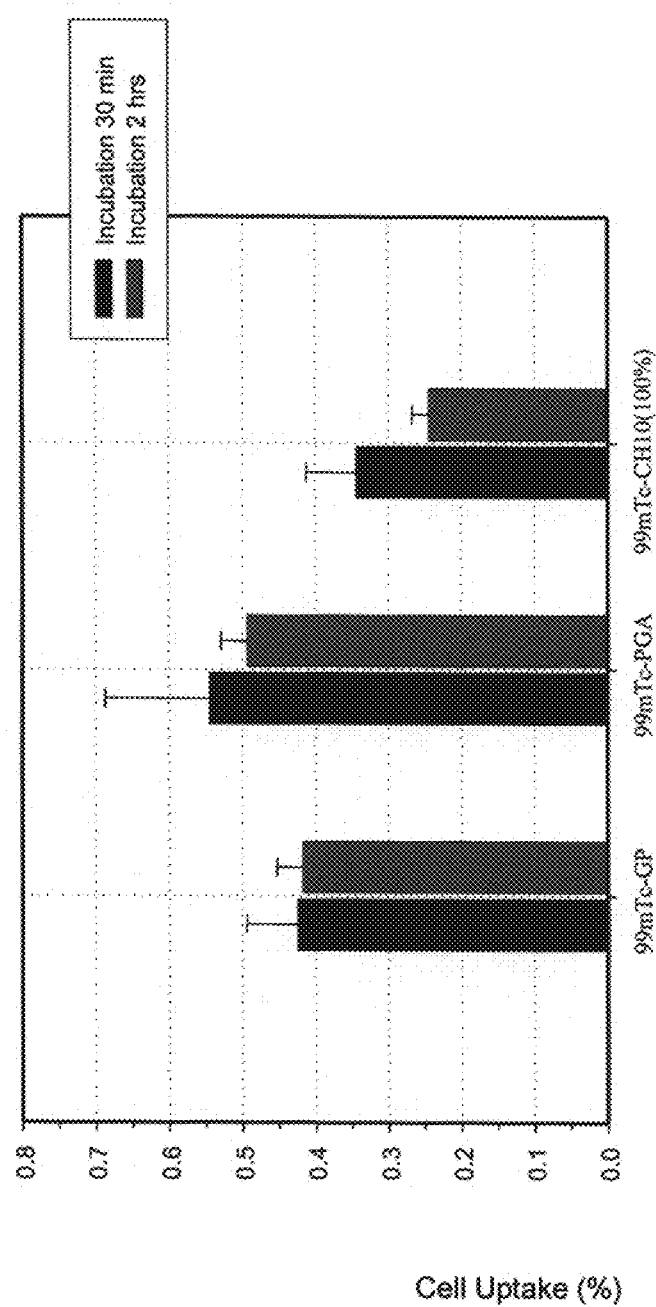
FIG. 5 shows the cellular uptake of $^{99m}$Tc-GP, $^{99m}$Tc-PGA and $^{99m}$Tc-CH(100%) by mammary tumor cells in vitro.

To evaluate whether glycopeptides have tumor targeting potential, mammary tumor cell line (13762) was selected. The cells were plated to 12 well tissue culture plates at a density of 50,000 cells per well. The cells were incubated with 4 µCi (0.148 MBq) of $^{99m}$Tc-labeled glycopeptide (GP), poly(glutamic acid) (PGA), chitosan (CH10, 50%), or chitosan (CH10) (100 µg/well). The structures of the agents tested are shown in FIG. 4. Cells were incubated with radiotracers at 37° C. at 0.5-2 hrs. After incubation, cells were washed with ice-cold phosphate-buffered saline (PBS) twice and trypsinized with 0.5 ml of trypsin solution. Then cells were collected and the radioactivity was measured by gamma counter. Data are expressed in mean±SD percent uptake ratio of three measurements. There was similar cellular uptake between glycopeptide and PGA (FIG. 5). However, glycopeptide is preferred in actual biological systems because it targets both vascular tissue and cellular receptors, unlike PGA with targets cells alone.

Example 5: Tumor Scintographic Imaging Studies

To demonstrate whether glycopeptide could specifically target tumor tissue, a group of female Fischer 344 tumor-bearing (right leg) rats with or without turpentine-induced inflammation (left leg) were administered with 300 µCi of $^{99m}$Tc-labeled glycopeptide, chitosan (50% and 100%), or poly(glutamic acid) (PGA). Scintographic images, using a gamma camera equipped with low-energy, parallel-hole collimator, were obtained at 0.5, 2 and 4 hrs. The tumor could be visualized well at all times. Tumor-to-muscle and tumor-to-inflammation ratios in glycopeptide group as compared to peptide and chitosan groups were higher at 0.5-3 hrs. Selected images are shown in FIG. 6.

Cellular uptake assays indicated that glycopeptide and glutamate peptide had higher uptake (0.4-0.5%) than chitosan (0.2%). Biodistribution of $^{99m}$Tc-glycopeptide in breast tumor-bearing rats showed increased tumor-to-tissue count density ratios as a function of time. Planar images confirmed that the tumors could be visualized clearly. At 2 hrs, tumor/muscle ratios for glycopeptide, glutamate peptide and chitosan were 3.9, 3.0 and 4.89. Although tumor/muscle rations are higher for chitosan alone, use of the glycopeptide is preferred because it targets both cells and vasculature. Additionally, glycopeptide exhibits better tissue retention overall.

Example 6: Tumor Response to Paclitaxil Treatment

To assess anti-angiogenic treatment response, rats were treated with paclitaxel (40 mg/kg,iv), followed by imaging with $^{99m}$Tc-glycopeptide on day 4. Tumor uptake and in situ hybridization (ISH) and TUNEL assays were conducted pre- and post-paclitaxel treatment.

In rats treated with paclitaxel, no marked tumor progression was observed compared to $^{99m}$Tc-glycopeptide baseline on day 4. Tumor necrosis was clearly seen post-treatment. There was a correlation between tumor uptake and cellular targets expression as demonstrated by ISH and TUNEL assays.

Example 7: Bone Scintographic Imaging Studies

Figure 7:
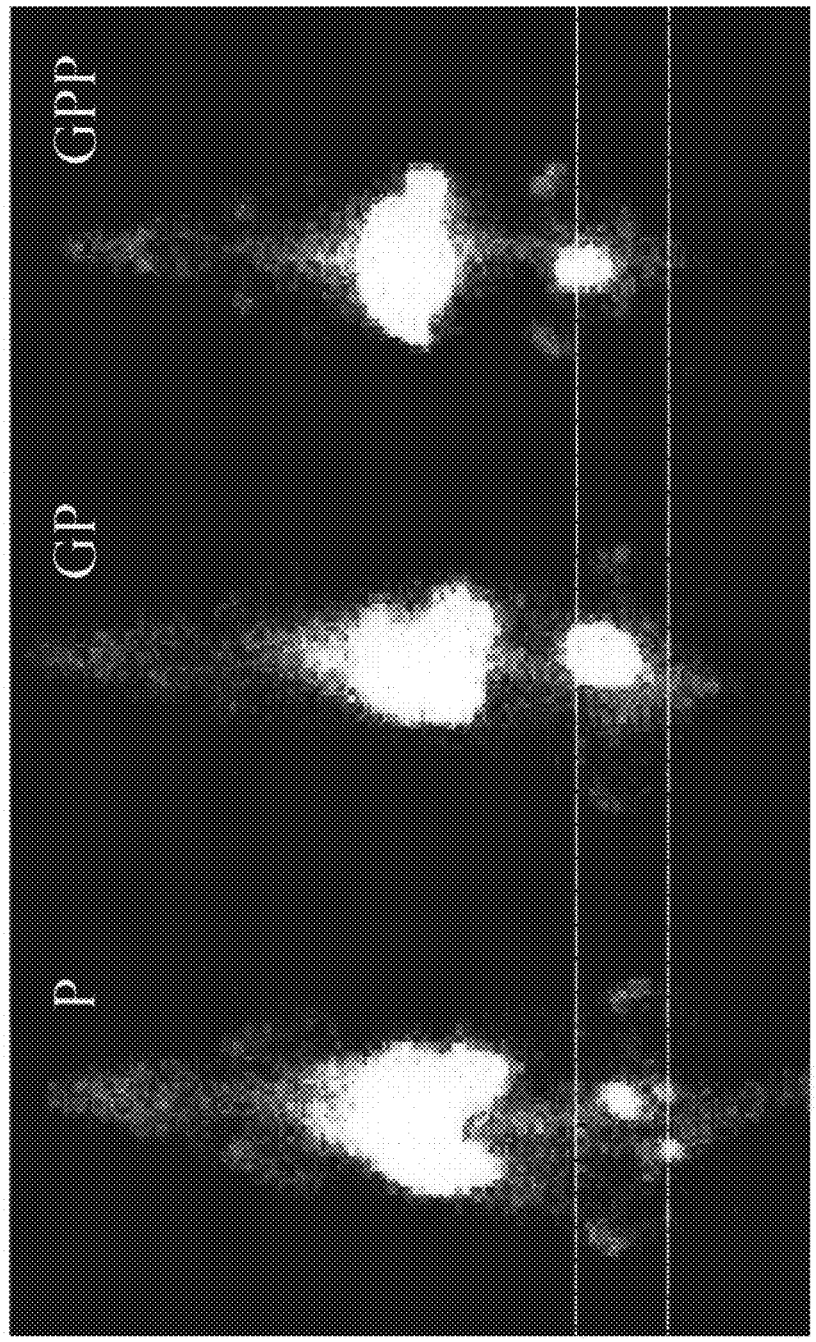
FIG. 7 shows the results of assays for cellular uptake in bone in vivo. Planar scintography of $^{99m}$Tc-Pamidronate (P), $^{99m}$Tc-Glycopeptide (GP), $^{99m}$Tc-Glycopeptide-Pamidronate (GPP) was performed 120 minutes after injection. (300 µCi/rat, i.v. injection, acquired 500,000 count).
Figure 8:
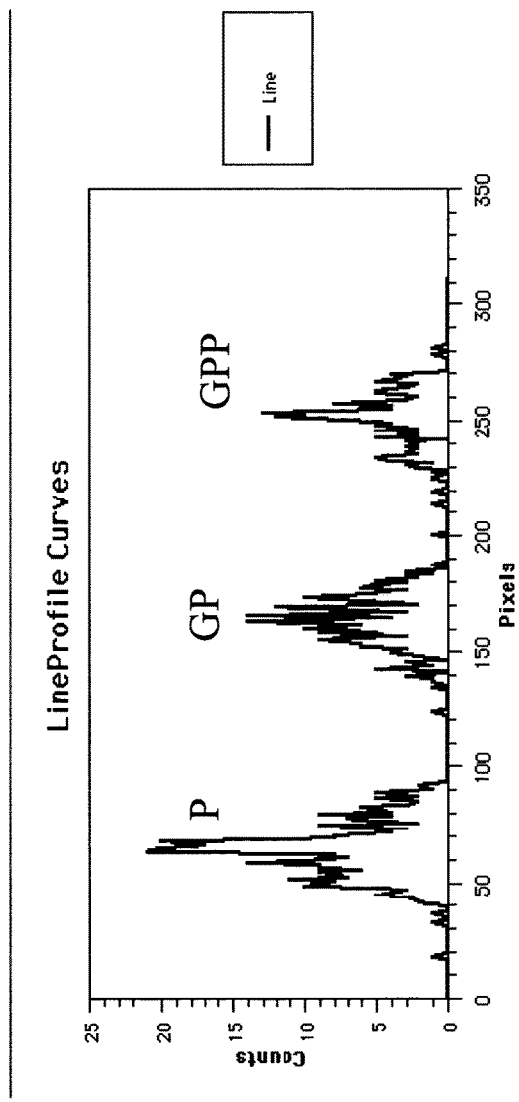
FIG. 8 also shows the results of assays for cellular uptake in bone in vivo. A line profile demonstration of $^{99m}$Tc-Pamidronate (P), $^{99m}$Tc-Glycopeptide (GP), $^{99m}$Tc-Glycopeptide-Pamidronate (GPP) was performed 120 minutes after injection. (300 µCi/rat, i.v. injection, acquired 500,000 count).

To demonstrate glycopeptide could be used to target bone, normal female Fischer 344 rats (125-175 g) were administered with 300 µCi of $^{99m}$Tc-labeled pamidronate, the glycopeptide and glycopeptide-pamidronate conjugate. Glycopeptide-pamidronate was able to target bone (FIGS. 7 and 8).

Example 8: Bone Loss Prevention

Glycopeptide-pamidronate conjugate, glycopeptide, or pamidronate will be administered in various dosages to female rate whose ovaries have previously been removed. Oovarectomy is strongly correlated with osteoporosis-like bone loss in rats. This bone loss may be observed over a period of several months. Because glycopeptide-pamidronate conjugate exhibits bone-targeting tendencies, it is expected that its administration will lessen or prevent oovarectomy-associated bone loss in female rats. Further, because pamidronate targets bone poorly, improved results are expected when using the glycopeptide conjugate as opposed to pamidronate alone.

Although the present invention and its advantages have been described in detail, it should be understood that various changes, substitutions and alternations can be made herein without departing from the spirit and scope of the invention as defined by the following claims.

The invention claimed is:
1. A glycopeptide targeting a tumor tissue comprising:
a chitosan moiety;
a poly(glutamic acid) or poly(aspartic acid) moiety comprising carboxyl groups;
a therapeutic agent; and
a metal,
wherein the chitosan moiety is covalently bonded to the poly(glutamic acid) or poly(aspartic acid) moiety via an amide bond,
wherein the therapeutic agent is conjugated to the chitosan through a carboxylic acid via a peptide bond linkage, and wherein the metal is a radionuclide and is conjugated to the carboxyl groups of the poly(glutamic acid) or poly(aspartic acid);

wherein the glycopeptide exhibits preferential affinity for a tumor tissue relative to bone tissue.

2. The glycopeptide of claim 1, wherein the glycopeptide comprises the poly(glutamic acid) or poly(aspartic acid) moiety in an amount of from about 5% to about 50% by weight of the glycopeptide.

3. The glycopeptide of claim 1, wherein the chitosan moiety has a molecular weight of from about 3,000 daltons to about 10,000 daltons, and wherein the poly(glutamic acid) or poly(aspartic acid) moiety has a molecular weight of from about 750 daltons to about 3,000.

4. The glycopeptide of claim 1, wherein the glycopeptide has a molecular weight of at least about 10,000 daltons.

5. The glycopeptide of claim 1, wherein the therapeutic agent is selected from the group consisting of: anticancer drugs, rheumatoid arthritis drugs, anticoagulants, anti-angiogenesis drugs, apoptosis drugs, steroids, anti-inflammatory drugs, and any combinations thereof.

6. The glycopeptide of claim 1, wherein the therapeutic agent comprises methotrexate.

7. The glycopeptide of claim 1, wherein the metal is selected from the group consisting of: Tc-99m, Cu-60, Cu-61, Cu-62, Cu-67, In-111, Tl-201, Ga-67, Ga-68, As-72, Re-186, Re-188, Ho-166, Y-90, Sm-153, Sr-89, Gd-157, Bi-212, and Bi-213, and any combinations thereof.

8. The glycopeptide of claim 1, wherein the glycopeptide comprises the therapeutic agent in an amount of from about 10% to about 60% by weight of the glycopeptide.

9. The glycopeptide of claim 1, wherein the chitosan moiety targets vascular endothelial cells and the poly(glutamic acid) or poly(aspartic acid) moiety targets cancer cells.

10. A method of producing a glycopeptide comprising:
combining chitosan and poly(glutamic acid) or poly(aspartic acid) in the presence of a carbodiimide and an acid group activator to form an amide bond between the chitosan and poly(glutamic acid) or poly(aspartic acid); and forming an amide or ester bond between the chitosan or poly(glutamic acid) or poly(aspartic acid) and a diagnostic or therapeutic agent.

11. The method of claim 10, further comprising conjugating a chelating agent and a metal to the chitosan or poly(glutamic acid) or poly(aspartic acid).

12. A glycopeptide targeting a tumor tissue comprising:
a chitosan moiety;
a poly(glutamic acid) or a poly(aspartic acid) moiety comprising carboxyl groups; and
a metal,
wherein the chitosan moiety is covalently bonded to the poly(glutamic acid) or poly(aspartic acid) moiety via an amide bond,
wherein the metal is a radionuclide and is conjugated to the carboxyl groups of the poly(glutamic acid) or poly(aspartic acid), and wherein said glycopeptide exhibits preferential affinity for a tumor tissue relative to bone tissue.

13. The glycopeptide of claim 12, wherein the glycopeptide comprises the poly(glutamic acid) or poly(aspartic acid) moiety in an amount of from about 5% to about 50% weight of the glycopeptide.

14. The glycopeptide of claim 12, wherein the chitosan moiety has molecular weight of from about 3,000 daltons to about 10,000 daltons, and wherein the poly(glutamic acid) or poly(aspartic acid) moiety has a molecular weight of from about 750 daltons to about 3000.

15. The glycopeptide of claim 12, wherein the glycopeptide has a molecular weight of at least about 10,000 daltons.

16. The glycopeptide of claim 12, wherein the metal is selected from the group consisting of: Tc-99m, Cu-60, Cu-61, Cu-62, Cu-67, In-111, Tl-201, Ga-67, Ga-68, As-72, Re-186, Re-188, Ho-166, Y-90, Sm-153, Sr-89, Gd-157, Bi-212, and Bi-213, and any combinations thereof.

* * * * *